(12) United States Patent
Meggiolan et al.

(10) Patent No.: US 10,274,030 B2
(45) Date of Patent: Apr. 30, 2019

(54) BRAKE DISC FOR A BICYCLE

(71) Applicant: CAMPAGNOLO S.r.l., Vicenza (IT)

(72) Inventors: Mario Meggiolan, Creazzo (IT);
Davide Zenere, Vicenza (IT)

(73) Assignee: CAMPAGNOLO S.R.L., Vicenza (IT)

( * ) Notice: Subject to any disclaimer, the term of this patent is extended or adjusted under 35 U.S.C. 154(b) by 0 days.

(21) Appl. No.: 15/637,904

(22) Filed: Jun. 29, 2017

(65) Prior Publication Data
US 2018/0010658 A1    Jan. 11, 2018

(30) Foreign Application Priority Data

Jul. 5, 2016   (IT) .............................. UA2016A4917

(51) Int. Cl.
*F16D 65/12*   (2006.01)
*B62L 1/00*   (2006.01)
(Continued)

(52) U.S. Cl.
CPC ............ *F16D 65/125* (2013.01); *B62K 23/06* (2013.01); *B62L 1/005* (2013.01); *B62M 9/131* (2013.01); *B62M 25/04* (2013.01); *F16D 65/123* (2013.01); *F16D 65/02* (2013.01); *F16D 2065/1304* (2013.01); *F16D 2065/1316* (2013.01); *F16D 2200/003* (2013.01); *F16D 2200/0021* (2013.01)

(58) Field of Classification Search
CPC ................... F16D 65/123; F16D 65/02; F16D 2065/1304; F16D 2065/1316; F16D 2065/134; F16D 2065/1356; F16D 2065/1364

USPC .......................................................... 188/26
See application file for complete search history.

(56) References Cited

U.S. PATENT DOCUMENTS 6,964,323 B2 *  11/2005  Campbell ............... B62L 1/005
                                                  188/18 A
7,665,584 B2    2/2010   Hirotomi
(Continued)

FOREIGN PATENT DOCUMENTS

DE       102005033765 A1    1/2007
EP           1932753 A2    6/2008
(Continued)

OTHER PUBLICATIONS

Italian Search Report and Written Opinion in Italian Application No. UA2016A004917, dated May 18, 2017, with English translation.

*Primary Examiner* — Thomas J Williams
(74) *Attorney, Agent, or Firm* — Volpe and Koenig, P.C.

(57) ABSTRACT

A brake disc having a first component made of a first material, a braking track configured to cooperate with brake pads, and a second component made of a second material and having (i) a radially inner annular portion for coupling with a hub of a bicycle wheel and (ii) a plurality of radially outer portions for connecting to the first component at a respective plurality of connection portions of the first component. The first component comprises a plurality of connection arms that extend from the braking track towards the predetermined rotation axis (X) and that are distinct from the plurality of connection portions, wherein at least one of the connection arms of the first component and at least one of the radially outer connection portions of the second component are coupled together through at least one shape coupling.

16 Claims, 4 Drawing Sheets

(51) Int. Cl.
*B62M 9/131* (2010.01)
*B62M 25/04* (2006.01)
*B62K 23/06* (2006.01)
*F16D 65/02* (2006.01)

(56) References Cited

U.S. PATENT DOCUMENTS

| | | | |
|---|---|---|---|
| 9,206,869 B2 * | 12/2015 | Wen | F16D 65/847 |
| D784,873 S * | 4/2017 | Kobayashi | D12/180 |
| 10,030,726 B1 | 7/2018 | Wang | |
| 2005/0139432 A1 * | 6/2005 | Takizawa | F16D 65/123 188/26 |
| 2005/0230199 A1 * | 10/2005 | Takizawa | B62L 1/005 188/218 XL |
| 2006/0054422 A1 | 3/2006 | Dimsey et al. | |
| 2011/0240420 A1 * | 10/2011 | Souwa | F16D 65/12 188/218 XL |
| 2012/0000736 A1 | 1/2012 | Koshiyama | |
| 2013/0240309 A1 * | 9/2013 | Moore | F16D 65/12 188/218 XL |
| 2015/0345577 A1 | 12/2015 | Watarai | |
| 2017/0328428 A1 * | 11/2017 | Taniguchi | F16D 65/121 |
| 2017/0370430 A1 | 12/2017 | Dunlap | |
| 2018/0010657 A1 * | 1/2018 | Meggiolan | F16D 65/125 |

FOREIGN PATENT DOCUMENTS

| | | | | |
|---|---|---|---|---|
| EP | 2821663 A2 | 1/2015 | | |
| GB | 1371158 A | * | 10/1974 | F16D 13/72 |

* cited by examiner

BRAKE DISC FOR A BICYCLE

CROSS REFERENCE TO RELATED APPLICATIONS

This application claims the benefit of Italian Application No. UA2016A004917, filed on Jul. 5, 2016, which is incorporated herein by reference as if fully set forth.

FIELD OF INVENTION

The present invention relates to a brake disc for a bicycle.

In particular, the brake disc is configured to be mounted on a hub of a bicycle wheel. Preferably, said bicycle is a racing bicycle.

BACKGROUND

As known, it is now common in bicycles to use disc brakes. Such brakes are indeed often preferred to conventional brakes of different design since they ensure a high braking force and are less subject to problems caused by mud or water.

Typically, a disc brake comprises a caliper fixed to the frame of the bicycle and a brake disc mounted on the hub of the wheel. Inside the caliper there are two or four opposite brake pads. The brake disc rotates inside the space defined between the opposite pads. By actuating the brake lever, the pads are brought towards the brake disc, generating friction on the brake disc and, consequently, braking the wheel.

The brake disc comprises a braking track configured to cooperate with pads and a radially inner annular portion for coupling with the hub.

The braking track is made of a material that ensures good braking characteristics, for example it can be made from steel.

The brake disc can be made in a single piece or, in order to reduce the weight thereof, it can be made in two components.

In this case, the brake disc comprises a first component having the braking track and a second component having the radially inner annular portion for coupling with the hub.

The first component is made of a first material that ensures good braking characteristics, like for example steel, whereas the second component is made of a lighter second material, like for example aluminum or light alloys.

The second component has a plurality of radially outer portions for connecting to the first component at a respective plurality of connection portions of the first component.

In the jargon, the second component is called spider, whereas the first component is simply indicated with the expression "braking track".

The connection between the radially outer connection portions of the second component and the connection portions of the first component can be fixed or, alternatively, can be such as to allow a relative radial and/or axial movement between the first and the second component.

Such relative movement is useful to stop the thermal dilations of the first component that occur during use (by the friction generated by the contact between pads and braking track) creating undesired stresses at the connection areas between first component and second component.

As far as the coupling with the hub is concerned, the radially inner annular portion of the brake disc (which is made in the second component, in the case of a brake disc made in two components) is provided with a grooved radially inner surface (i.e. a radially inner surface that extends longitudinally and is provided with longitudinal grooves), which is mounted on a matching grooved radially outer surface (i.e. a radially outer surface that extends longitudinally and is provided with longitudinal grooves matching those of the radially inner surface) of a portion of the hub, as is disclosed in patent application EP 1932753 to the same Applicant.

EP 1932753 also discloses a lock nut, which is screwed onto the hub until it comes into axial abutment on the radially inner annular portion of the brake disc, so as to define the axial portion of the brake disc on the hub.

The Applicant has observed that, in the case of a brake disc made in two components, it is necessary for the connection between the radially outer connection portions of the second component and the connection portions of the first component to be extremely reliable, so that a certain braking quality is guaranteed as much as possible.

Damage to or breaking of the connections between first and second component could result in great limitations in braking quality, even to the point of braking itself being impossible, with the obvious serious consequences in terms of safety.

The above becomes even more important, if such a thing is possible, in the field of racing bicycles.

The problem at the basis of the present invention is to make a brake disc for a bicycle that, as well as having excellent features of strength and lightness, ensures extreme certainty of braking over time.

SUMMARY

The present invention relates to a bicycle brake disc that has predetermined rotation axis and is comprised of at least two components. A first component is made of a first material and has a braking track configured to cooperate with brake pads. The second component is made of a second material and has (i) a radially inner annular portion for coupling with a hub of a bicycle wheel and (ii) a plurality of radially outer portions for connecting to the first component at a respective plurality of connection portions of the first component. Wherein the first component comprises a plurality of connection arms that extend from the braking track towards the predetermined rotation axis and that are distinct from the plurality of connection portions, and at least one of the connection arms of the first component and at least one of the radially outer connection portions of the second component are coupled together through at least one shape coupling.

BRIEF DESCRIPTION OF THE DRAWING(S)

Further features and advantages of the invention will become clearer from the description of a preferred embodiment, made with reference to the attached drawings, where:

DETAILED DESCRIPTION OF THE PREFERRED EMBODIMENT(S)

Figure 1:
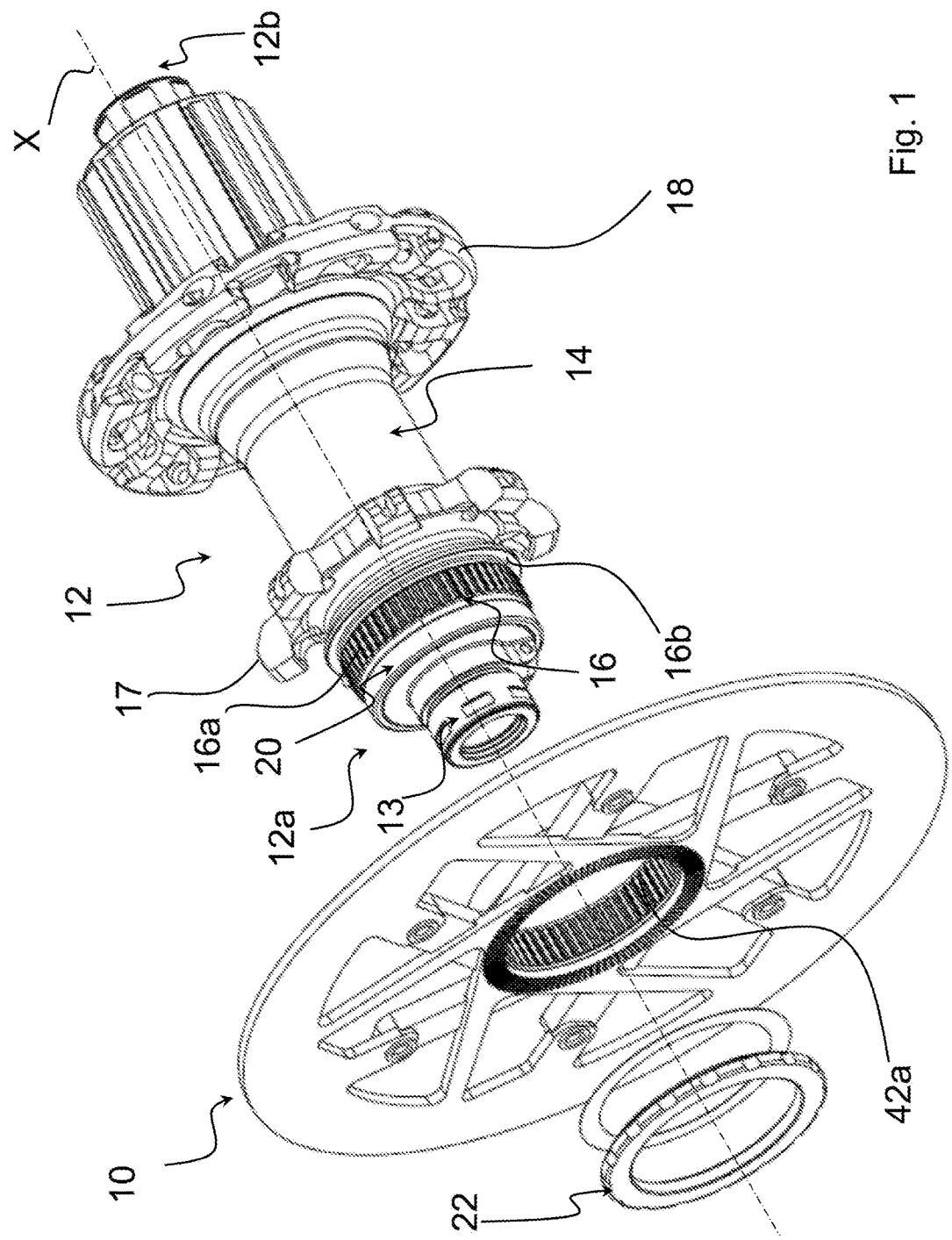
FIG. 1 is an exploded perspective view of a hub of a bicycle wheel, comprising a brake disc for a bicycle according to the present invention.

In the following description and claims, the terms "axial, "axially", "longitudinal', "longitudinally" and similar refer to a direction substantially coinciding with or substantially parallel to a rotation axis of the brake disc, which substantially coincides with a longitudinal axis of the hub, whereas the terms "radial", "radially" and similar refer to a direction that lies in a plane substantially perpendicular to the longitudinal rotation axis of the hub brake disc and that passes through such a longitudinal rotation axis of the hub.

The present invention therefore relates to a brake disc for a bicycle having predetermined rotation axis and comprising:

a first component made of a first material and having a braking track configured to cooperate with brake pads;

a second component made of a second material and having (i) a radially inner annular portion for coupling with a hub of a bicycle wheel and (ii) a plurality of radially outer portions for connecting to said first component at a respective plurality of connection portions of said first component;

characterized in that said first component comprises a plurality of connection arms that extend from said braking track towards said predetermined rotation axis and that are distinct from said plurality of connection portions, wherein at least one of said connection arms of said first component and at least one of said radially outer connection portions of said second component are coupled together through at least one shape coupling.

Advantageously, thanks to the provision of connection arms of the first component coupled together through the shape couplings with radially outer connection portions of the second component, the first and second component are kept coupled together even in the misfortunate case of damage to or breaking of the connection between the first and the second component at the radially outer connection portions of the second component and at the respective connection portions of the first component.

Indeed, the shape couplings between connection arms of the first component and radially outer connection portions of the second component allow the first and second component to remain rotationally substantially constrained to one another even in the misfortunate case of damage or breaking outlined above, without there being a significant relative rotation between first and second component, so as to ensure a sufficient possibility of braking, even if with lower efficiency with respect to normal operation of the undamaged or unbroken brake disc. However, in the case of damage or breaking outlined above, the cyclist can take care of replacing the brake disc as soon as possible to be able to have use of normal operation of the brake disc.

Advantageously, furthermore, the shape coupling does not require further structural elements, such as bolts, rivets, screws or similar, to be able to carry out its action.

Furthermore, the shape couplings between connection arms of the first component and radially outer connection portions of the second component also ensure a strengthening of the first component, so that the braking track of the first component withstands the stresses to which it is subjected during braking better than in brake discs of the prior art.

Furthermore, the connection arms of the first component that are distinct from the plurality of connection portions allow the two mutual constraint areas between the first and the second component to be mechanically and functionally decoupled. In this way, damage to or breaking of the connection between the first and the second component, at the radially outer connection portions of the second component and of the respective connection portions of the first component, does not jeopardize the rotational mechanical constraint between the first and the second component at the radially inner annular portions of the first and second component.

Hereinbelow preferred features of the brake disc for a bicycle according to the present invention are described, which can be foreseen individually or in combination with each other.

Preferably, said at least one shape coupling comprises at least one housing seat made on one from said at least one connection arm and said at least one radially outer connection portion and housing a portion of the other from said at least one connection arm and said at least one radially outer connection portion.

Advantageously, the housing seats can be made easily from the constructive point of view.

Preferably, said at least one connection arm and said at least one radially outer connection portion extend along directions of extension substantially crossing over one another.

Advantageously, the directions of extension substantially crossing over one another improve the structural characteristics of torsional strength of the brake disc, as well as also the substantial rotational constraint between the first and the second component.

Preferably, said at least one housing seat is made on said at least one radially outer connection portion of the second component and has an axial depth greater than or equal to half of an axial thickness of said at least one connection arm of said first component measured at said housing seat. More preferably, said at least one housing seat has an axial depth equal to the axial thickness of said at least one connection arm of said first component.

Advantageously, the aforementioned axial depths of the housing seat ensure a sufficient substantial rotational constraint between the first and the second component.

Preferably, said housing seat comprises at least one shoulder formed on said at least one radially outer connection portion of the second component abutted by a portion of said at least one connection arm of said first component, said shoulder having a direction of extension substantially parallel to a direction of extension of said at least one connection arm of said first component.

Preferably, said first component comprises a radially inner annular portion connected to said braking track through said plurality of connection arms.

More preferably, the brake disc comprises axial locking members active on the radially inner annular portions of the first and of the second component to keep said radially inner annular portions of the first and of the second component under mutual pressure.

Advantageously, thanks to the provision of the radially inner annular portion of the first component and of the axial locking members active on the radially inner annular portions of the first and second component, the first and second component are kept under mutual pressure even in the misfortunate case of damage to or breaking of the connection between the first and the second component at the radially outer connection portions of the second component and at the respective connection portions of the first component.

Indeed, the axial locking members keep the radially inner annular portions of the first and of the second component under mutual pressure, which by friction remain rotationally substantially constrained to one another even in the misfortunate case of damage or breaking outlined above, without there being a significant relative rotation between first and second component, so as to ensure a sufficient possibility of braking, even if with lower efficiency with respect to normal operation of the undamaged or unbroken brake disc.

Furthermore, thanks to the provision of the radially inner annular portion of the first component connected to the braking track through the plurality of connection arms, it is also ensured that there is strengthening of the first component, so that the braking track of the first component withstands the stresses to which it is subjected during braking better than in brake discs of the prior art.

Preferably, said axial locking members are furthermore configured to axially constrain said radially inner annular portion of the second component to said hub.

Advantageously, the axial locking members thus also define the axial position of the brake disc with respect to the hub.

Preferably, the axial locking members are in abutment against the radially inner annular portion of the first component.

More preferably, said radially inner annular portion of said first component is provided with a knurled axially outer surface.

Advantageously, the knurled axially outer surface makes it possible to increase the friction with the axial locking members in abutment against the radially inner annular portion of the first component.

Preferably, said radially inner annular portion of the first component at least partially juxtaposes the radially inner annular portion of the second component in the axial direction.

Advantageously, the greater the juxtaposition, the greater the friction between the radially inner annular portions of the first and second component, on which the axial locking members are active.

Preferably, said axial locking members comprise a collar in axial abutment on the radially inner annular portion of the first component and a lock nut, which extends axially away from the collar, configured to couple with said hub.

More preferably, said collar and said lock nut are made in one piece.

Preferably, said braking track, said plurality of connection arms, said plurality of connection portions and said radially inner annular portion of said first component have a substantially uniform axial thickness and are substantially coplanar.

Advantageously, the first component can be easily made from the constructive point of view.

Preferably, said first component is placed on an axially outer first mid-plane with respect to a second mid-plane of said second component, wherein said first and second planes are parallel to one another.

With reference now to the figures, reference numeral 10 wholly indicates a brake disc for a bicycle according to the present invention.

The brake disc 10 is configured to be mounted on a hub 12 of a bicycle wheel (not illustrated).

In particular, in the non-limiting example of FIG. 1 a hub 12 for a rear bicycle wheel is shown.

The hub 12 is mounted on the frame of the bicycle.

In particular, the frame comprises two opposite support arms of the rear wheel at the respective free end portions of which housing seats of opposite free end portions 12*a*, 12*b* of the hub 12 are foreseen.

A caliper (not illustrated) of a disc brake is fixed onto the bicycle frame.

In particular, the caliper is fixed in a conventional manner to one of the support arms of the rear wheel.

Inside the caliper there are at least two opposite brake pads (not illustrated).

The brake disc 10 rotates inside the space defined between the opposite brake pads. By actuating the brake lever (not illustrated), the brake pads are brought closer to the brake disc 10, generating friction on the brake disc 10 and, consequently, braking the wheel.

In particular, the hub 12 comprises a pin 13 extending along a longitudinal axis X of the hub 12 and a body 14 rotatably mounted on the pin 13. The longitudinal axis X coincides with the rotation axis of the bicycle wheel.

The body 14 comprises a coupling portion 16 with the brake disc 10. Furthermore, the body 14 comprises, in a position adjacent to such a coupling portion 16 and on the axially innermost side with respect to it, a further coupling portion 17 with a plurality of spokes of the wheel (not shown). The coupling portions 16 and 17 are preferably portions of a single body. Alternatively, the coupling portions 16 and 17 can be defined in two distinct bodies.

On the body 14, on the axially opposite side with respect to the coupling portions 16 and 17, a flange 18 is fitted comprising a coupling portion with the remaining spokes of the wheel, which are arranged on the opposite side to the aforementioned plurality of spokes with reference to a mid-plane of the rim of the wheel, such a plane being perpendicular to the rotation axis of the wheel. Such a flange 18 can be an integral part of the body 14.

A pair of rolling bearings (not illustrated) is radially arranged between the pin 13 and the body 14 and allows the rotation of the body 14 with respect to the pin 13. The bearings are mounted in a position adjacent to the opposite free end portions of the pin 13.

The coupling portion 16 comprises a disc seat 16*a*, for receiving and locking in rotation the brake disc 10, and a shoulder 16*b*, which provides an abutment position in the axial direction for the brake disc 10 mounted on the disc seat 16*a*.

The disc seat 16*a* comprises a grooved radially outer surface, namely a radially outer surface that extends longitudinally and is provided with longitudinal grooves.

The brake disc 10 comprises a grooved radially inner surface 42*a* matching that of the disc seat 16*a* (namely a radially inner surface 42*a* that extends longitudinally and is provided with longitudinal grooves matching those of the grooved radially outer surface of the disc seat 16*a*), as will be described better hereinafter.

More in general, the disc seat 16*a* is shaped according to a shape coupling profile. This term is meant to indicate that the profile of the disc seat 16*a* has geometric characteristics such as to allow the transmission of a torsion between the body 14 (on which the disc seat 16*a* is formed) and the brake disc 10 mounted on such a disc seat 16*a* with a matching profile. A shape coupling profile can for example be a polygonal profile, or a circular profile with an alteration (for example, levelled along a rope), or other. In particular, the shape coupling profile of the disc seat 16*a* illustrated in the non-limiting example of the figures is a grooved profile, with projections and throats, oriented in a direction parallel to the axis X.

The shoulder 16*b* is provided adjacent to an axially inner side of the disc seat 16*a*.

Adjacent to the opposite axially outer side of the disc seat 16*a* there is a threaded portion 20, formed at a free end portion of the body 14, for coupling with a lock nut 22, which holds the brake disc 10 in the disc seat 16*a*, against the shoulder 16*b*.

Figure 2:
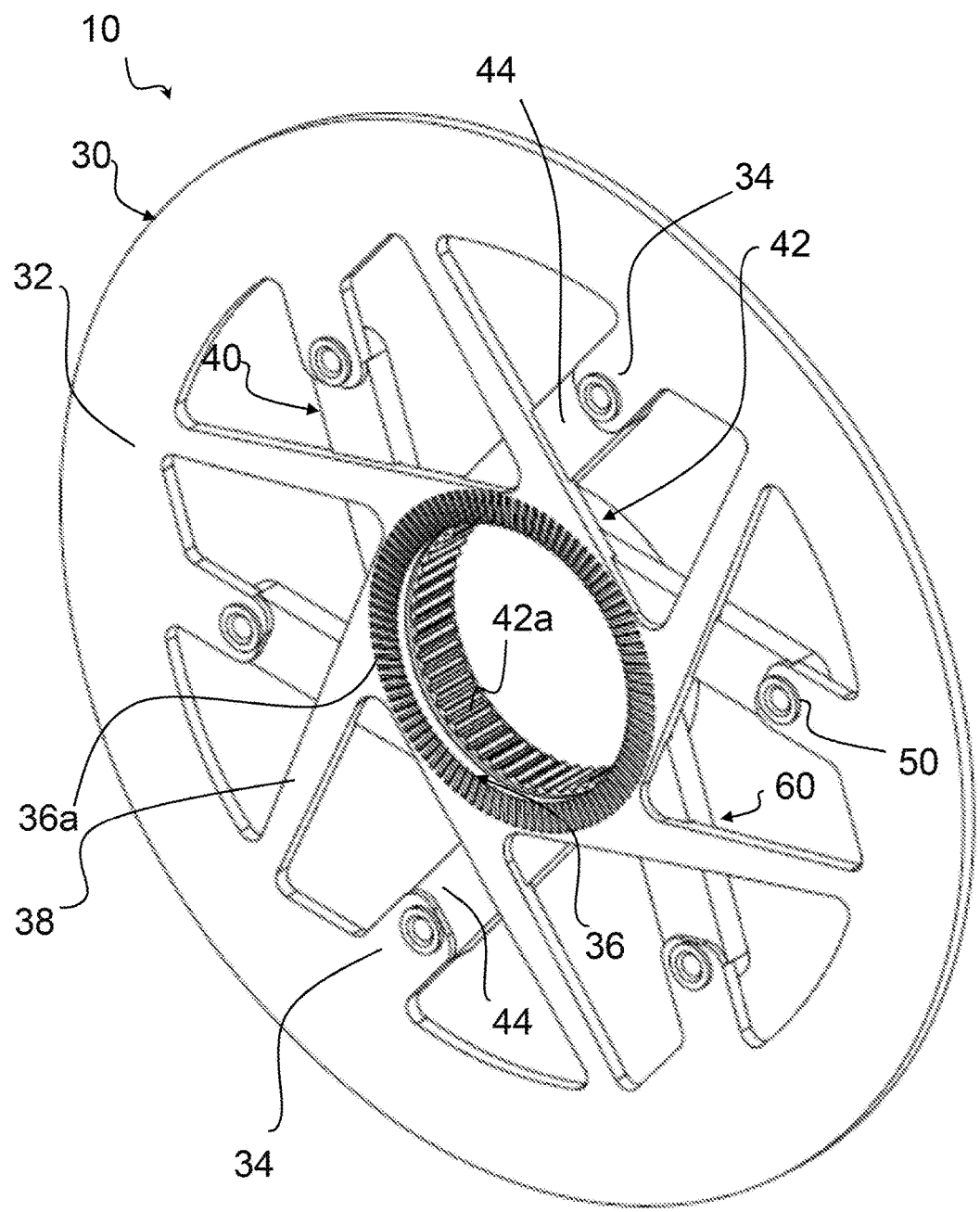
FIG. 2 is a perspective view of the brake disc of FIG. 1.
Figure 3:
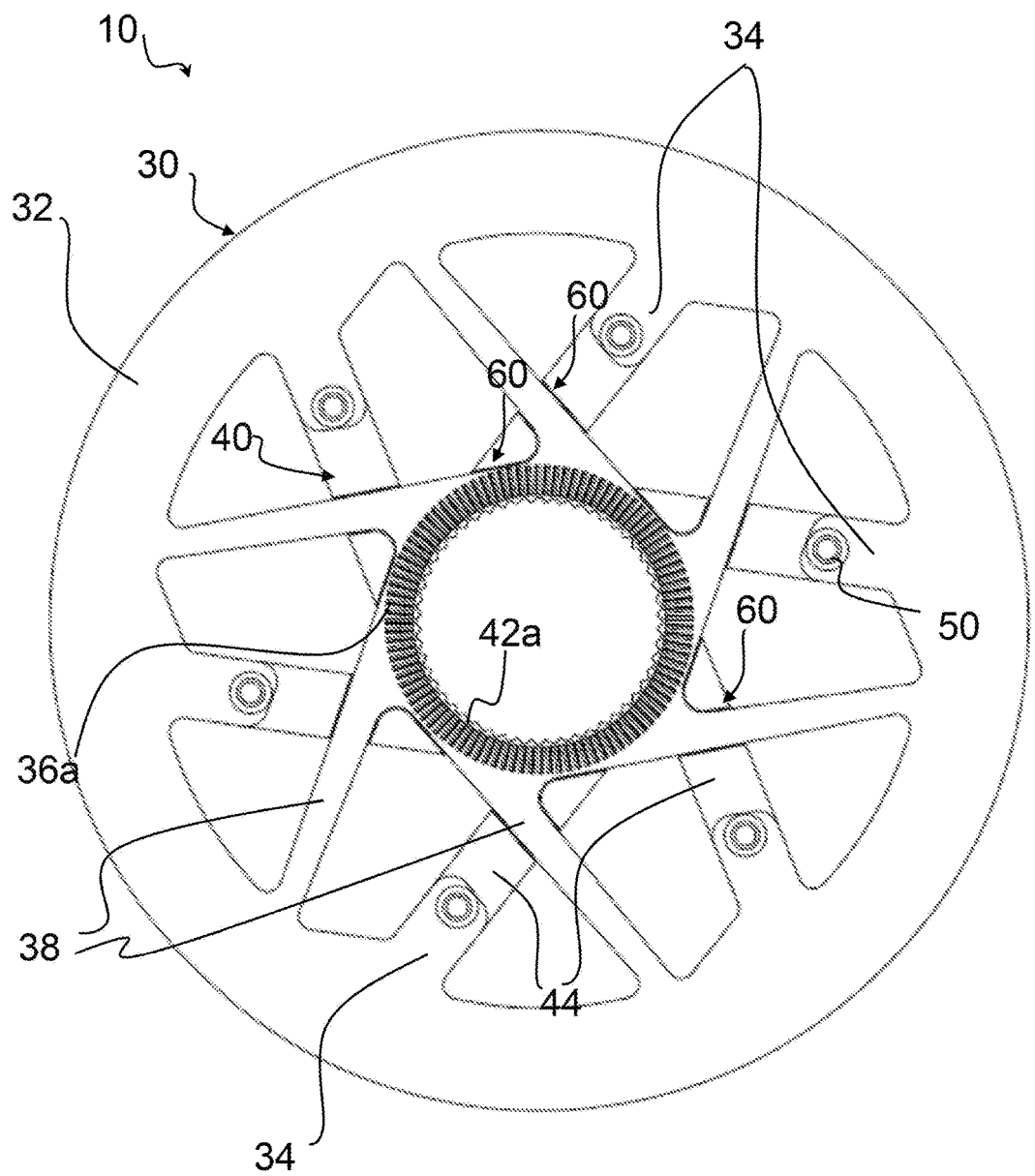
FIG. 3 is a front view of the brake disc of FIG. 1.
Figure 4:
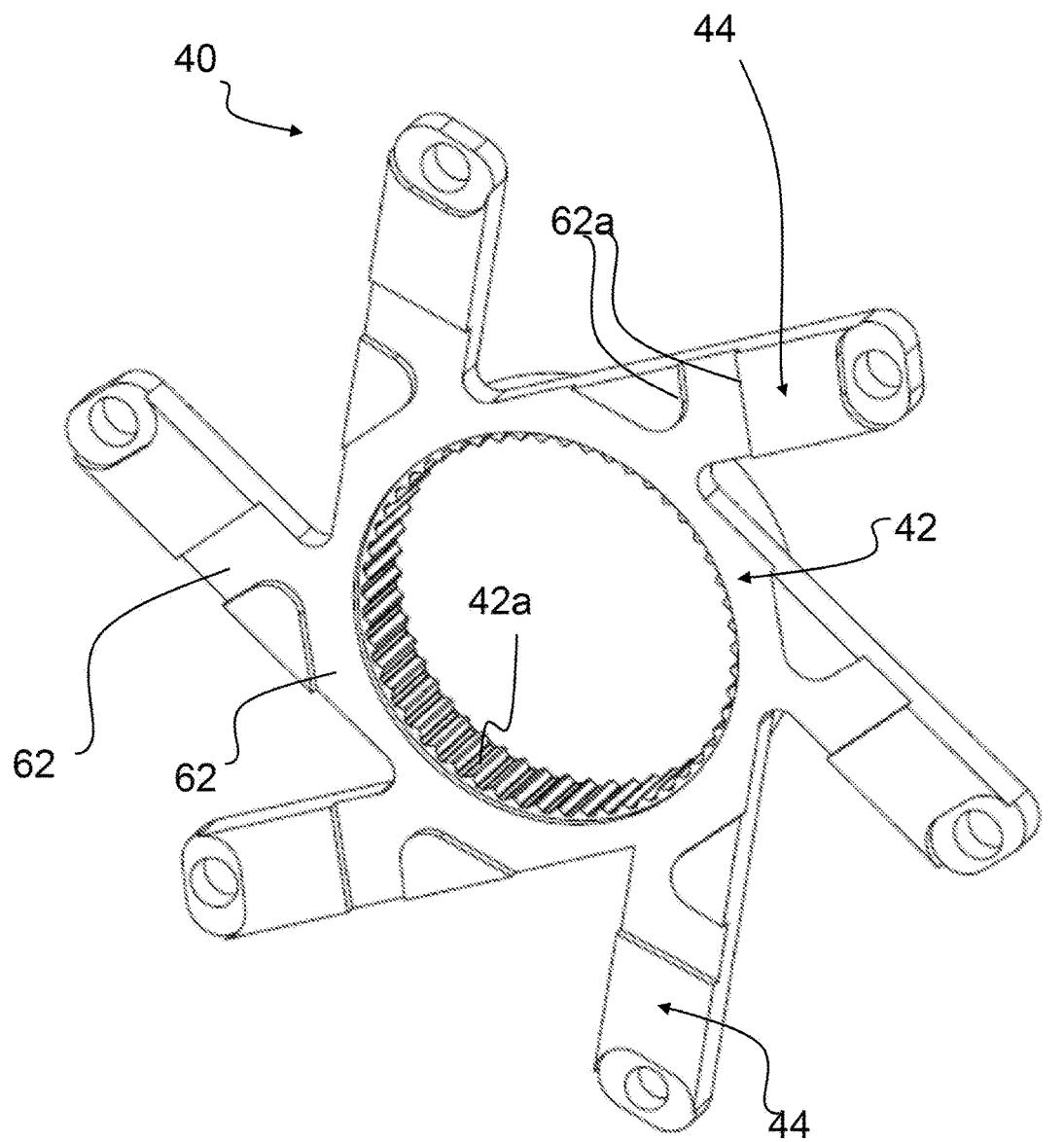
FIG. 4 is a perspective view of a component of the brake disc of FIG. 1.

Now with particular reference to FIGS. 2-4, the brake disc 10, having rotation axis coinciding with the longitudinal axis X of the hub 12, comprises a first component 30 and a second component 40.

The first component 30 comprises a braking track 32 and the second component 40 comprises a radially inner annular portion 42 for coupling with the hub 12. The braking track 32 has substantially annular extension. The radially inner annular portion 42 is provided with the grooved radially inner surface 42a described earlier.

The first component 30 is made of a first material that ensures good braking characteristics, like for example steel, whereas the second component 40 is made of a lighter second material, like for example aluminum or light alloys.

The second component 40 comprises a plurality of radially outer portions 44 for connecting to the first component 30 at a respective plurality of connection portions 34 of the first component 30. In the non-limiting example illustrated in the figures, the radially outer portions 44 and the connection portions 34 are circumferentially equally spaced and are six in number. In the figures, so as not to complicate the graphical representation, reference numerals are only indicated on some of the radially outer portions 44 and the connection portions 34, as well as only some of other elements described hereinafter.

The connection between the radially outer connection portions 44 of the second component 40 and the connection portions 34 of the first component 30 can be fixed or, alternatively, be such as to allow a relative radial and/or axial clearance between the first component 30 and the second component 40. In the non-limiting example illustrated in the figures, such a connection is made through caulked pins 50, received in respective holes formed in the radially outer portions 44 and in the connection portions 34.

The braking track 32 is configured to cooperate with the brake pads.

Advantageously, the first component 30 comprises a radially inner annular portion 36 connected to the braking track 32. The radially inner annular portion 36 could comprise a grooved radially inner surface, analogous to the grooved radially inner surface 42a of the second component 40. In the embodiment illustrated in the attached figures such a grooved radially inner surface of the radially inner annular portion 36 of the first component 30 is not provided.

In particular, the radially inner annular portion 36 is connected to the braking track 32 through a plurality of connection arms 38 distinct from the plurality of connection portions 34. In the non-limiting example illustrated in the figures, the connection arms 38 are circumferentially equally spaced and are six in number.

On the radially inner annular portions 36, 42 of the first 30 and of the second component 40 axial locking members are active, which keep the radially inner annular portions 36, 42 of the first 30 and of the second component 40 under mutual pressure.

In the non-limiting example illustrated in the figures, the axial locking members comprise the lock nut 22 described above.

In general, the axial locking members are furthermore configured to axially constrain the radially inner annular portion 42 of the second component 40 to the hub 12.

The axial locking members are in abutment against the radially inner annular portion 36 of the first component 30.

The radially inner annular portion 36 of the first component 30 is provided with a knurled axially outer surface 36a.

The radially inner annular portion 36 of the first component 30 at least partially juxtaposes the radially inner annular portion 42 of the second component 40 in the axial direction. In the non-limiting example illustrated in the figures, the radially inner annular portion 36 substantially entirely juxtaposes the radially inner annular portion 42 in the axial direction.

The axial locking members preferably comprise a collar in axial abutment on the radially inner annular portion 36 of the first component 30 and the lock nut 22, which extends axially away from the collar, configured to couple with the hub 14.

In the non-limiting example illustrated in FIG. 1, the collar is made in one piece with the lock nut 22.

Advantageously, the connection arms 38 of the first component 30 and the radially outer connection portions 44 of the second component 40 are coupled together through shape couplings 60.

In the non-limiting example illustrated in the figures, shape couplings 60 are provided on all of the connection arms 38 and on all of the radially outer connection portions 44. Alternatively, shape couplings 60 can be provided only on one or some of the connection arms 38 and radially outer connection portions 44.

In particular, the shape coupling 60 comprises one or more housing seats 62 made on the radially outer connection portion 44 and housing a portion of the connection arm(s) 38. Alternatively, vice-versa, one or more housing seats 62 can be made on the connection arms 38 and house a portion of the radially outer connection portion(s) 44.

In the non-limiting example illustrated in the figures, on each radially outer connection portion 44 there are two housing seats 62 for two consecutive connection arms 38 of the first component 30.

Preferably, the housing seats 62 are provided on axially outer surfaces of the radially outer connection portions 44.

In particular, the housing seats 62 comprise shoulders 62a formed on the radially outer connection portion 44 of the second component 40 abutted by a portion of the connection arm 38 of the first component 30. The shoulders 62a have directions of extension substantially parallel to directions of extension of the connection arms 38 of the first component 30 that are housed in the respective housing seats 62.

In the non-limiting example illustrated in the figures, the connection arms 38 and the radially outer connection portion 44 extend along directions of extension substantially crossing over one another. Preferably, the angle formed between a connection arm 38 and a radially outer connection portion 44 is comprised between 45° and 110°, more preferably comprised between 70° and 100°, for example about 80°.

In particular, the connection arms 38 of the first component 30 extend from the radially inner annular portion 36 along substantially tangential directions and, in the front view of the brake disc 10 illustrated in FIG. 3, are directed in the counter-clockwise direction. Vice-versa, the radially outer connection portions 44 of the second component 40 extend from the radially inner annular portion 42 along substantially tangential directions and, in the front view of the brake disc 10 illustrated in FIG. 3, are directed in the clockwise direction.

Preferably, the housing seats 62 have an axial depth greater than or equal to half of an axial thickness of the connection arms 38 of the first component 30, measured at the housing seat 62.

Preferably, the first component 30 has a substantially uniform axial thickness, for example comprised in a range of between about 1.8 mm and 2 mm.

Preferably, the braking track 32, the connection arms 38, the connection portions 34 and the radially inner annular portion 36 are substantially coplanar.

The first component 30 is arranged on an axially outer first mid-plane with respect to a second mid-plane of the second component 40, wherein such first and second planes are parallel to each other.

Preferably, at the area of juxtaposition between the radially inner annular portion 36 of the first component 30 and the radially inner annular portion 42 of the second component 40, the second component 40 comprises a groove directed axially having a depth equal to the depth of the housing seats 62.

In this way it is possible to ensure a uniform thickness of the first component 30, the contact of the radially inner annular portion 36 of the first component 30 on the radially inner annular portion 42 of the second component and the insertion of the connection arms 38 in the housing seats 62.

In the non-limiting example illustrated in the figures, the connection arms 38 have a shorter transverse width than the transverse width of the connection portions 34 of the first component 30, which have a transverse width substantially equal to that of the radially outer connection portions 44 of the second component 40.

The ratio between the transverse width of the connection arms 38 and that of the connection portions 34 is for example comprised in a range of between about 0.4 and 0.7.

In terms of sizing of the brake disc 10, the following considerations are valid.

During braking, the brake pads act on the braking track 32 as a heat flow source, which is in part conveyed away by convection, in part transmitted by conduction towards the center of the brake disc 10 and to the hub 12.

A radial temperature gradient is created in the brake disc 10 from the hottest point (outer edge of the brake disc 10) to the least hot point (inner edge of the brake disc 10). Such a gradient generates a deformation of the brake disc 10 and a relative inner tensional state, since the brake disc 10 is constrained to the hub 12.

The brake disc 10 of the invention comprises the connection arms 38 made entirely in the first material of the first component 30 and other arms formed from the connection portions 34, made in the first material of the first component 30, connected through caulked pins 50 to the radially outer connection portions 44, made in the second material of the second component 40.

In order to obtain the maximum thermal stability of the brake disc 10, it is suitable to size the length of the connection arms 38, of the connection portions 34 and of the radially outer connection portions 44 so that the radial deformation is as uniform as possible during braking.

Such lengths can be changed independently within a finite range, by modifying the angle of extension of each connection arm 38 and of each arm formed from the connection portions 34 connected to the radially outer connection portions 44 with respect to the radial direction.

Furthermore, for the connection portions 34 and the radially outer connection portions 44 it is possible to establish the point where the connection with the caulked pin 50 is made, namely the percentage of the total length made in the first material of the first component 30 (the remaining length is, consequently, made in the second material of the second component 40). Such a percentage of the total length made in the first material of the first component 30 can for example be comprised in a range between about 10° and 60°.

The sizing can be further improved by considering the contact heat resistance of the connections between first 30 and second component 40; in this way, the sizing can be made using a more realistic temperature profile.

Of course, those skilled in the art can bring numerous modifications and variants to the brake disc for a bicycle of the present invention, in order to satisfy specific and contingent requirements, all of which are in any case encompassed by the scope of protection defined by the following claims.

What is claimed is:

1. A brake disc for a bicycle having a predetermined rotation axis (X), the brake disc comprising:
   a first component made of a first material and having a braking track configured to cooperate with brake pads;
   a second component made of a second material and having (i) a radially inner annular portion for coupling with a hub of a wheel of the bicycle and (ii) a plurality of radially outer portions for connecting to said first component at a respective plurality of connection portions of said first component;
   wherein said first component comprises a plurality of connection arms that extend from said braking track towards said predetermined rotation axis (X) and that are distinct from said plurality of connection portions,
   wherein at least one of said connection arms of said first component and at least one of said radially outer connection portions of said second component are coupled together at a position different from a position of the plurality of connection portions through at least one shape coupling.

2. The brake disc according to claim 1, wherein said at least one shape coupling comprises at least one housing seat made on one from said at least one connection arm and said at least one radially outer connection portion and housing a portion of the other from said at least one connection arm and said at least one radially outer connection portion.

3. The brake disc according to claim 2, wherein said at least one connection arm and said at least one radially outer connection portion extend along directions of extension substantially crossing over one another.

4. The brake disc according to claim 2, wherein said at least one housing seat is made on said at least one radially outer connection portion of the second component and has an axial depth greater than or equal to half of an axial thickness of said at least one connection arm of said first component measured at said housing seat.

5. The brake disc according to claim 4, wherein said housing seat comprises at least one shoulder formed on said at least one radially outer connection portion of the second component abutted by a portion of said at least one connection arm of said first component, said shoulder having a direction of extension substantially parallel to a direction of extension of said at least one connection arm of said first component.

6. The brake disc according to claim 1, wherein said first component comprises a radially inner annular portion connected to said braking track through said plurality of connection arms.

7. The brake disc according to claim 6, comprising axial locking members active on the radially inner annular portions of the first and of the second component to keep said radially inner annular portions of the first and of the second component under mutual pressure.

8. The brake disc according to claim 7, wherein said axial locking members are furthermore configured to axially constrain said radially inner annular portion of the second component to said hub.

9. The brake disc according to claim 7, wherein the axial locking members are in abutment against the radially inner annular portion of the first component.

10. The brake disc according to claim 6, wherein said radially inner annular portion of said first component is provided with a knurled axially outer surface.

11. The brake disc according to claim 6, wherein said radially inner annular portion of the first component at least partially juxtaposes the radially inner annular portion of the second component in an axial direction.

12. The brake disc according to claim 7, wherein said axial locking members comprise a collar in axial abutment on the radially inner annular portion of the first component and a lock nut, which extends axially away from the collar, configured to couple with said hub.

13. The brake disc according to claim 12, wherein said collar and said lock nut are made in one piece.

14. The brake disc according to claim 6, wherein said braking track, said plurality of connection arms, said plurality of connection portions and said radially inner annular portion of said first component have a substantially uniform axial thickness and are substantially coplanar.

15. The brake disc according to claim 1, wherein said first component is arranged on an axially outer first mid-plane with respect to a second mid-plane of said second component, wherein said first and second planes are parallel to one another.

16. A brake disc for a bicycle having a predetermined rotation axis (X), the brake disc comprising:
   a first component made of a first material and having a braking track configured to cooperate with brake pads;
   a second component made of a second material and having (i) a radially inner annular portion for coupling with a hub of a wheel of the bicycle and (ii) a plurality of radially outer portions for connecting to said first component at a respective plurality of connection portions of said first component;
   wherein said first component comprises a plurality of connection arms that extend from said braking track towards said predetermined rotation axis (X) and that are distinct from said plurality of connection portions,
   wherein at least one of said connection arms of said first component and at least one of said radially outer connection portions of said second component are coupled together through at least one shape coupling,
   wherein said at least one shape coupling comprises at least one housing seat made on one from said at least one connection arm and said at least one radially outer connection portion and housing a portion of the other from said at least one connection arm and said at least one radially outer connection portion.

* * * * *